United States Patent
Shener-Irmakoglu et al.

(10) Patent No.: US 10,806,480 B2
(45) Date of Patent: Oct. 20, 2020

(54) MEDICAL DEVICE

(71) Applicant: Smith & Nephew, Inc., Memphis, TN (US)

(72) Inventors: Cemal Shener-Irmakoglu, Woburn, MA (US); Rafal Z. Jezierski, Middleton, MA (US); Brian Joseph Loreth, Braintree, MA (US)

(73) Assignee: SMITH & NEPHEW, INC., Memphis, TN (US)

( * ) Notice: Subject to any disclaimer, the term of this patent is extended or adjusted under 35 U.S.C. 154(b) by 581 days.

(21) Appl. No.: 15/590,136

(22) Filed: May 9, 2017

(65) Prior Publication Data
US 2017/0238957 A1 Aug. 24, 2017

Related U.S. Application Data

(62) Division of application No. 13/075,327, filed on Mar. 30, 2011, now Pat. No. 9,668,762.

(51) Int. Cl.
| | | |
|---|---|---|
| *A61B 17/32* | (2006.01) | |
| *A61B 90/00* | (2016.01) | |
| *A61B 17/00* | (2006.01) | |

(52) U.S. Cl.
CPC .............. *A61B 17/32002* (2013.01); *A61B 2017/0023* (2013.01); *A61B 2017/00477* (2013.01); *A61B 2090/0814* (2016.02); *A61B 2217/005* (2013.01); *Y10T 29/49826* (2015.01)

(58) Field of Classification Search
CPC ...... A61B 17/32002; A61B 2017/0023; A61B 2017/00477; Y10T 29/49826
See application file for complete search history.

(56) References Cited

U.S. PATENT DOCUMENTS

| | | |
|---|---|---|
| 4,696,308 A | 9/1987 | Meller et al. |
| 4,826,490 A | 5/1989 | Byrne et al. |
| 5,104,379 A | 4/1992 | Nakamura et al. |
| 5,149,322 A | 9/1992 | Nash |
| 5,492,527 A | 2/1996 | Glowa et al. |
| 5,743,883 A | 4/1998 | Visconti |

(Continued)

FOREIGN PATENT DOCUMENTS

| | | |
|---|---|---|
| EP | 788775 | 8/1997 |
| EP | 1386587 | 2/2004 |

(Continued)

OTHER PUBLICATIONS

Office Action for Mexican Patent Application No. MX/a/2013/011273; dated Jul. 11, 2017, 3 pages.
Office Action for Japanese Patent Application No. 2016-502652; dated Dec. 25, 2017; 3 pages.
Office Action for Japanese Patent Application No. 2016-241088; dated Oct. 2, 2017, 2 pages.

(Continued)

*Primary Examiner* — Daniel L Cerioni
*Assistant Examiner* — Raymond P Dulman

(57) ABSTRACT

A medical device that includes an outer tube assembly that includes a straight outer tube, an inner tube assembly that includes a straight inner tube disposed within the outer tube, and at least one interference member on the outer tube assembly and at least one interference member on the inner tube assembly. The inner tube and the outer tube are configured to rotate relative to each other to resect tissue at a distal end of the inner and outer tubes. The interference members are configured to prevent a force exerted along a longitudinal axis of the inner tube from separating the inner and outer tubes without rendering the medical device unusable.

8 Claims, 7 Drawing Sheets

(56) References Cited

U.S. PATENT DOCUMENTS

| | | | |
|---|---|---|---|
| 5,871,493 | A | 2/1999 | Sjostrom et al. |
| 5,957,947 | A | 9/1999 | Wattiez et al. |
| 7,479,117 | B2 | 1/2009 | Zadow |
| 2002/0165549 | A1 | 11/2002 | Owusu-Akyaw et al. |
| 2002/0198466 | A1 | 12/2002 | Alberico |
| 2003/0023256 | A1 | 1/2003 | Estes et al. |
| 2004/0092992 | A1 | 5/2004 | Adams et al. |
| 2005/0267502 | A1 | 12/2005 | Hochman |
| 2006/0025814 | A1 | 2/2006 | Hatori |
| 2007/0239065 | A1 | 10/2007 | Zadow |
| 2008/0195103 | A1 | 8/2008 | Lewis et al. |
| 2008/0275481 | A1 | 11/2008 | Scarpone |
| 2010/0072251 | A1 | 3/2010 | Baxter, III et al. |
| 2010/0204722 | A1 | 8/2010 | Gilsdorf |
| 2010/0286694 | A1 | 11/2010 | Rio et al. |

FOREIGN PATENT DOCUMENTS

| | | |
|---|---|---|
| RU | 2089225 | 9/1997 |
| RU | 2528966 | 9/2014 |
| WO | 9716124 | 9/1997 |

OTHER PUBLICATIONS

Office Action in Japanese Patent Application No. 2014-502652, dated Aug. 5, 2016.
Office Action in Russian Patent Application No. 2013146852/14(072735).
Search Report for PCT Application No. MX/a/2013/011273, dated May 26, 2016.
Office Action in Russian Application No. 2013146852/14; dated Jan. 22, 2016.
Examination Report No. 2 in Australian Patent Application No. 2012236842, dated Feb. 11, 2016.
P.R. of China Second Office Action for Chinese Application No. 201280026340.0, dated Jan. 19, 2016.
P.R. of China First Office Action for Chinese Application No. 201280026340.0, dated Jun. 26, 2015.
International Search Report and Written Opinion for International Application No. PCT/US2012/030506, dated Jun. 19, 2012.
Office Action for Mexican Patent Application No. MX/a/2013/011273; dated Jan. 13, 2017, 3 pages.
Office Action for European Patent Application No. 12712833.8-1664; dated Feb. 6, 2017; 4 pages.
Office Action for Mexico Patent Application No. MX/a/2013/011273; dated Jan. 18, 2018; 3 pages.
Indian Application No. 8315/DELNP/2013 Examination Report.

MEDICAL DEVICE

CROSS-REFERENCE TO RELATED APPLICATIONS

This application is a divisional application of U.S. application Ser. No. 13/075,327 filed Mar. 30, 2011 and titled "Medical Device" (now U.S. Pat. No. 9,668,762), which application is incorporated by reference herein as if reproduced in full below.

TECHNICAL FIELD

This document relates to a medical device.

BACKGROUND

Some medical devices used to resect tissue have a tube-in-tube construction. In such a construction, an inner tube is disposed within an outer tube, and the tubes are designed to rotate relative to one another (for example, the inner tube is designed to rotate while the outer tube remains stationary). In some designs, the proximal end of both the inner and the outer tube can include cutting edges between which the tissue is disposed and sheared. In other designs, the proximal end of the inner tube can include a burr that shears the tissue.

SUMMARY

In one aspect, a medical device includes an outer tube assembly that includes a straight outer tube, an inner tube assembly that includes a straight inner tube disposed within the outer tube, and at least one interference member on the outer tube assembly and at least one interference member on the inner tube assembly. The inner tube and the outer tube are configured to rotate relative to each other to resect tissue at a distal end of the inner and outer tubes. The interference members are configured to prevent a force exerted along a longitudinal axis of the inner tube from separating the inner and outer tubes without rendering the medical device unusable.

This, and other aspects, can include one or more of the following features. The inner tube assembly can include an inner tube hub and the at least one interference member on the inner tube assembly can include a groove formed on an outer surface of the inner tube hub. The outer tube assembly can include an outer tube hub and the at least one interference member on the outer tube assembly can include at least one retaining member that interferes with the groove to prevent the force from separating the inner and outer tubes. The retaining member can include one or more pins extending through the outer tube hub to interfere with the groove. The outer tube hub can include one or more holes through which the one or more pins extend. The retaining member can include an indentation formed on an outer surface of the outer tube hub. The indentation can form a protrusion on an inner surface of the outer tube hub that interferes with the groove to prevent the force from separating the inner and outer tubes.

The inner tube assembly can include an inner tube hub and the at least one interference member on the inner tube assembly can include an inclined ridge formed on an outer surface of the inner tube hub. The outer tube assembly can include an outer tube hub and the at least one interference member on the outer tube assembly can include a snap mechanism that protrudes toward an inner portion of the outer tube hub. The inclined ridge and the snap mechanism can be configured to allow the inclined ridge to move past the snap mechanism when at least a portion of the inner tube assembly is inserted into the outer tube assembly and to interfere after the inner tube assembly is inserted within the outer tube assembly such that the force exerted along the longitudinal axis is prevented from separating the inner and outer tubes. The snap mechanism can be elastically deformable to accommodate the ridge when at least the portion of the inner tube assembly is inserted into the outer tube assembly.

The inner tube assembly can include an inner tube hub and the at least one interference member on the inner tube assembly can include a snap mechanism formed on an outer surface of the inner tube hub. The outer tube assembly can include an outer tube hub. The at least one interference member on the outer tube assembly can include a step feature formed on an inner surface of the outer tube hub to retain the snap mechanism after the inner tube assembly is inserted within the outer tube assembly such that the force exerted along the longitudinal axis is prevented from separating the inner and outer tubes.

The inner tube assembly can include an inner tube hub and the at least one interference member on the inner tube assembly can include a first groove formed on an outer surface of the inner tube hub and a ring attached to the first groove. The outer tube assembly can include an outer tube hub and the at least one interference member on the outer tube assembly can include a second groove formed on an inner surface of the outer tube hub. The ring can be configured to compress to allow the ring attached to the first groove to be inserted into the outer tube assembly, and to expand into the second groove and interfere to prevent the force exerted along the longitudinal axis from separating the inner and outer tubes. The ring can be a split ring.

The outer tube assembly can include an outer tube hub and the at least one interference member on the outer tube assembly can include multiple step features and a groove, each formed on an inner surface of the outer tube hub. The inner tube assembly can include an inner tube hub, and the at least one interference member on the inner tube assembly can include a ridge formed on an outer surface of the inner tube hub, and a seal flange attached to the inner tube hub. The ridge can engage a first step feature and the seal flange can engage a second step feature when the seal flange and at least a portion of the inner tube assembly are inserted into the outer tube assembly. The ridge and the seal flange can interfere to prevent the force exerted along the longitudinal axis from separating the inner and outer tubes.

The inner tube assembly can include an inner tube hub, and the at least one interference member on the inner tube assembly can include a groove formed on an outer surface of the straight inner tube and a retaining ring positioned in the groove. The outer tube assembly can include an outer tube hub and the at least one interference member on the outer tube assembly can include an inner wall of the outer tube hub. The retaining ring can include an edge that interferes with the outer tube hub to prevent the force from separating the inner and outer tubes.

The device can include a hub attached to a proximal end of the inner tube assembly, and an extension attached to the hub, and configured to couple the inner tube assembly and the hub to a drive unit configured to rotate the inner tube and the outer tube relative to each other. The device can include an opening on the distal end of the outer tube, and a burr to resect tissue on the distal end of the inner tube. The device can include a first cutting surface on the distal end of the outer tube, and a second cutting surface on the distal end of the inner tube that cooperates with the first cutting surface to resect tissue.

In another aspect, a method of producing a medical device includes forming an outer tube assembly that includes a straight outer tube and a first interference member, forming an inner tube assembly that includes a straight inner tube and a second interference member, and engaging the inner tube assembly with the outer tube assembly such that the inner tube is disposed within the outer tube. The inner tube and the outer tube are configured to rotate relative to each other to resect tissue at a proximal end of the inner and outer tubes. The first and second interference members are configured to prevent a force exerted along a longitudinal axis of the inner tube from separating the inner and outer tubes without rendering the medical device unusable.

This, and other aspects, can include one or more of the following features. The inner tube assembly and the outer tube assembly can include an inner tube hub and an outer tube hub, respectively. Forming the inner tube assembly that includes the straight inner tube and the second interference member can include forming a groove on an outer surface of the inner tube hub. Forming the outer tube assembly that includes the straight outer tube and the first interference member can include forming one or more holes through the outer tube hub. Engaging the inner tube assembly with the outer tube assembly such that the inner tube is disposed within the outer tube can include extending at least one retaining member through the one or more holes in the outer tube hub to interfere with the groove to prevent the force from separating the inner and outer tubes.

Forming the inner tube assembly that includes the straight inner tube and the second interference member can include forming a groove on an outer surface of the inner tube hub. Forming the outer tube assembly that includes the straight outer tube and the first interference member can include forming an indentation on an outer surface of the outer tube hub. The indentation can form a protrusion on an inner surface of the outer tube hub. Engaging the inner tube assembly with the outer tube assembly such that the inner tube is disposed within the outer tube can include engaging the indentation and the groove such that the protrusion interferes with the groove to prevent the force from separating the inner and outer tubes.

Forming the inner tube assembly that includes the straight inner tube and the second interference member can include forming an inclined ridge on an outer surface of the inner tube hub. Forming the outer tube assembly that includes the straight outer tube and the first interference member can include forming a snap mechanism that protrudes toward an inner portion of the outer tube hub. Engaging the inner tube assembly with the outer tube assembly such that the inner tube is disposed within the outer tube can include inserting the inclined ridge past the snap mechanism such that the inclined ridge interferes with the snap mechanism to prevent the force from separating the inner and outer tubes.

Forming the inner tube assembly that includes the straight inner tube and the second interference member can include forming a snap mechanism on an outer surface of the inner tube hub. Forming the outer tube assembly that includes the straight outer tube and the first interference member can include forming a step feature on an inner surface of the outer tube hub. Engaging the inner tube assembly with the outer tube assembly such that the inner tube is disposed within the outer tube can include inserting the snap mechanism past the step feature such that the snap mechanism interferes with the step feature to prevent the force from separating the inner and outer tubes.

Forming the inner tube assembly that includes the straight inner tube and the second interference member can include forming a first groove on an outer surface of the inner tube hub. Forming the outer tube assembly that includes the straight outer tube and the first interference member can include forming a second groove on an inner surface of the outer tube hub. Engaging the inner tube assembly with the outer tube assembly such that the inner tube is disposed within the outer tube can include attaching a compressible ring to the first groove and inserting the inner tube assembly into the outer tube assembly such that the ring expands into the second groove and interferes to prevent the force from separating the inner and outer tubes.

Forming the inner tube assembly that includes the straight inner tube and the second interference member can include forming a ridge on an outer surface of the inner tube hub. Forming the outer tube assembly that includes the straight outer tube and the first interference member can include forming multiple step features on an inner surface of the outer tube hub. Engaging the inner tube assembly with the outer tube assembly such that the inner tube is disposed within the outer tube can include attaching a seal flange to the inner tube hub and inserting at least a portion of the inner tube assembly into the outer tube assembly such that the ridge engages a first step feature and the seal flange engages a second step feature, and interfere to prevent the force from separating the inner and outer tubes.

Forming the inner tube assembly that includes the straight inner tube and the second interference member can include forming a groove on an outer surface of the inner tube hub. Forming the outer tube assembly that includes the straight outer tube and the first interference member can include forming an inner wall in the outer tube hub. Engaging the inner tube assembly with the outer tube assembly such that the inner tube is disposed within the outer tube can include attaching a retaining ring that includes an edge to the groove and inserting the inner tube assembly into the outer tube assembly such that the edge interferes with the outer tube hub to prevent the force from separating the inner and outer tubes.

A hub can be attached to a proximal end of the inner tube. The hub can have an extension configured to couple the inner tube assembly and the hub to a drive unit configured to rotate the inner tube and the outer tube relative to each other.

A further innovative aspect of the subject matter described here can be implemented as a medical device including an outer tube assembly that includes a straight outer tube, an inner tube assembly that includes a straight inner tube disposed within the outer tube, the inner tube and outer tube being configured to rotate relative to each other to resect tissue at a distal end of the inner and outer tubes, and means for preventing the inner tube from being removed from the outer tube without rendering the medical device unusable.

Particular implementations can include one or more of the following advantages. The medical device may be a single-use device. For instance, the medical device may be designed and constructed such that the removal of the inner tube from the outer tube after assembly is not possible without breaking components of the device and rendering the device unusable. Therefore, the tubes cannot be feasibly separated for sterilization or, even if the inner and outer tubes were removed, cleaned, and sterilized, the tubes nevertheless cannot be practically (or economically) re-assembled for another use. Consequently, in such a situation, the device is a single-use device.

The details of one or more embodiments of the subject matter described in this specification are set forth in the accompanying drawings and the description below. Other features, aspects, and advantages of the subject matter will become apparent from the description, the drawings, and the claims.

DETAILED DESCRIPTION

Figure 1A:
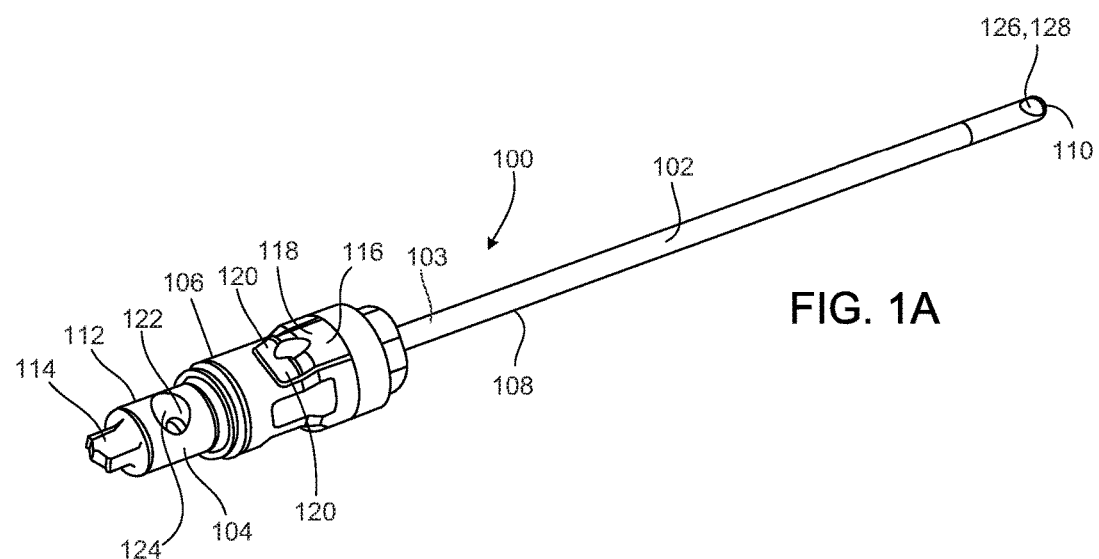
FIGS. 1A, 1B, and 1C are views of a medical device.
Figure 1B:
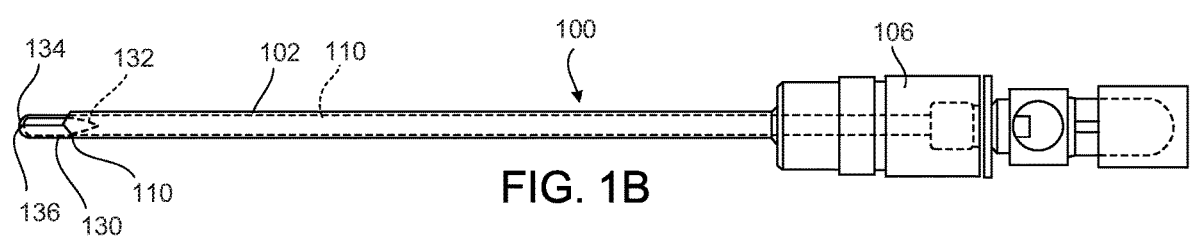
Figure 2:
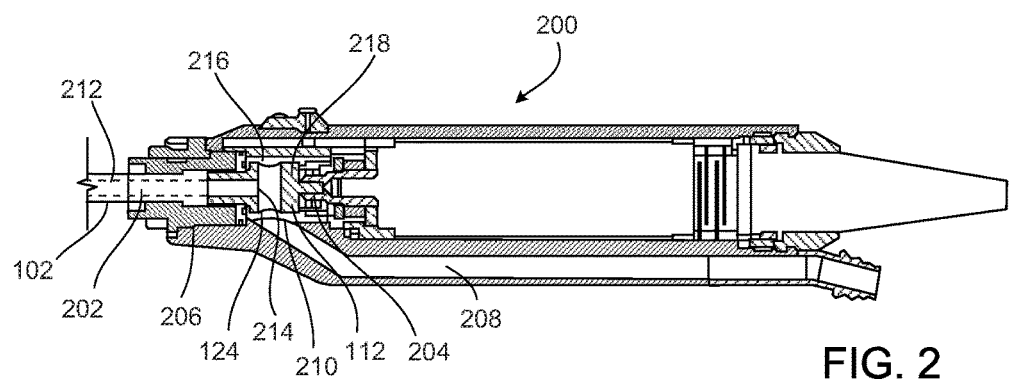
FIG. 2 is a cross-sectional view the medical device of FIG. 1 coupled to a handpiece.

Referring to FIGS. 1A, 1B and 2, a medical device is shown that is used to resect tissue using a tube-in-tube construction that shears tissue disposed between cutting edges of an outer non-rotating tube 102 and an inner rotating tube 110 of a rotary cutter 100. In the embodiment shown, the outer tube 102 and inner tube 110 are straight tubes, but other embodiments may employ tubes that are not straight (for example, curved tubes).

As described further below, the medical device is constructed to prevent the separation of the inner tube 110 and the outer tube 102 when a force is applied to separate the inner tube 110 and the outer tube 102. If the force is less than a threshold force (for example, 25 lbf), then the inner tube 110 and the outer tube 102 cannot be separated. If the force is greater than the threshold force, the tubes can be separated, but cannot be re-assembled to its original condition, and the device is rendered unusable.

An outer tube assembly 103 includes an outer tube 102 which is connected to an outer tube hub 106 at a proximal region 108 of outer tube 102. Inner tube assembly 104, which is rotatably received in outer tube hub 106 and outer tube 102, includes an inner tube 110 located within outer tube 102. The inner tube assembly 104 defines an aspiration lumen 202 and connects to a hub 112 located in a proximal region of the inner tube assembly 104 and partially received within outer tube hub 106. Hub 112 includes an extension 114, which is coupled to a motor drive mechanism 204 that rotates inner tube assembly 104 relative to outer tube hub 106 and outer tube 102. Outer tube hub 106 includes a coupling in the form of a resilient latching mechanism 116 for connecting rotary cutter 100 to a handpiece 200. In particular, mechanism 116 includes a cantilevered resilient arm 118 with ramped latches 120 that engage an annular flange 206 in handpiece 200 to axially secure rotary cutter 100 to handpiece 200.

Handpiece 200 (FIG. 2) includes an aspiration channel 208 terminating at an aspiration opening 210 for applying suction to aspiration lumen 202 to remove fluid and cut tissue from a surgical site. Aspiration lumen 202 in tube 110 of inner tube assembly 104 has a proximal opening 122 that communicates with a through hole 124 in motor coupling 112. Suction is applied through aspiration channel 208 to draw material through a side-facing window 126 in outer tube 102 and a side-facing window 128 in inner tube 110, into lumen 202, and through lumen openings 214 and both ends of hole 216 to aspiration channel 208.

Figure 1C:
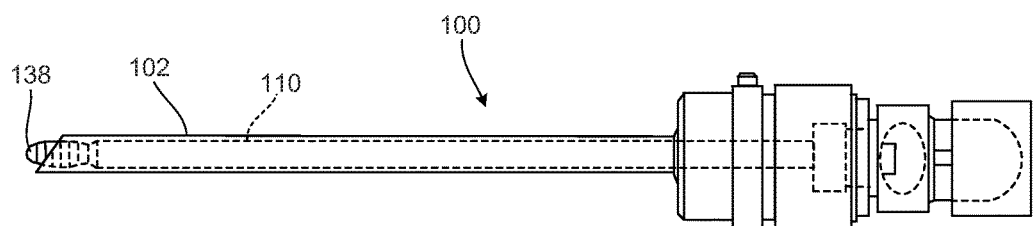

Referring to FIG. 1B, the medical device 100 includes a first cutting surface 134 on the distal end 130 of the outer tube 102 and a second cutting surface 132 on the distal end 136 of the inner tube 110 that cooperates with the first cutting surface to resect tissue. Referring to FIG. 1C, in alternative embodiments, the medical device 100 includes an opening on the distal end 130 of the outer tube 102 and a burr 138 to resect tissue on the distal end 136 of the inner tube 110 (FIG. 1B). A vacuum source (not shown) is coupled to the medical device 100 and vacuums the tissue, and the irrigating fluid surrounding the tissue, out of the instrument 100.

As noted above, the medical device 100 is constructed to prevent the separation of the inner tube 110 and the outer tube 102 without rendering the device unusable. In various embodiments, this is accomplished using interference members (not shown in FIGS. 1 and 2) on the inner tube assembly 104 and the outer tube assembly 103. The interference members are configured to prevent a force exerted along a longitudinal axis of the inner tube from separating the inner and outer tubes without rendering the medical device 100 unusable.

Figure 3:
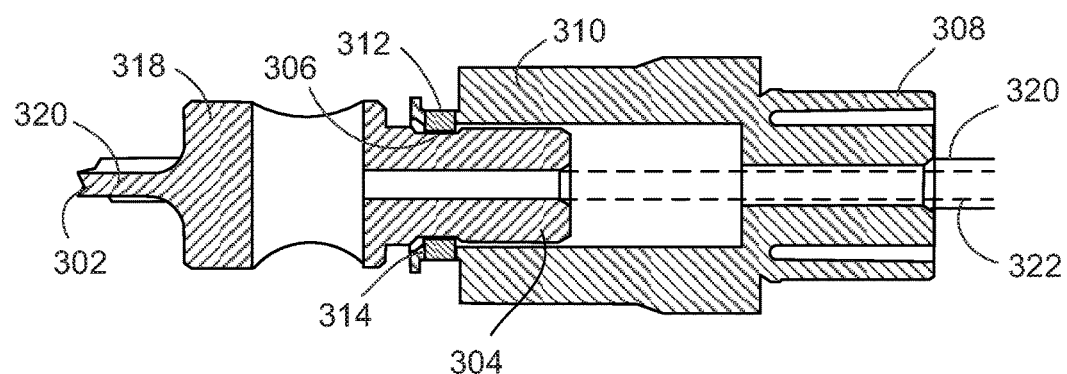
FIG. 3 is a cross-sectional view of a first embodiment of an inner tube assembly and an outer tube assembly with interference members.

FIG. 3 is a cross-sectional view of a first embodiment of an inner tube assembly 302 and an outer tube assembly 308 with interference members 306 and 312. The inner tube assembly 302 includes an inner tube 322, an inner tube hub 304, and an interference member 306, for example, a groove formed on an outer surface of the inner tube hub 304 at a proximal region of the inner tube hub 304. The outer tube assembly 308 includes an outer tube 320, an outer tube hub 310, and an interference member 312, for example, at least one retaining member, such as, one or more pins. The outer tube hub 310 includes one or more holes 314, formed on a distal region of the outer tube assembly 308, through which the interference member 312 (for example, the one or more pins) extend to a depth sufficient to interfere with the interference member 306 to prevent a force applied to the inner tube 322 or the outer tube 320 (or both) from separating the inner and outer tubes without rendering the medical device 100 unusable (for example, by breaking the portion of the outer tube assembly 310 through which the pins 312 extend).

Figure 4:
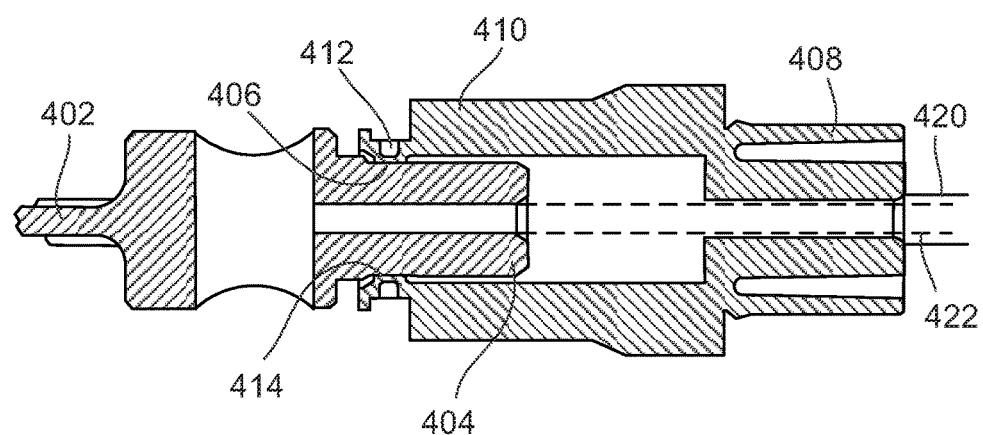
FIG. 4 is cross-sectional view of a second embodiment of an inner tube assembly and an outer tube assembly with interference members.

FIG. 4 is cross-sectional view of a second embodiment of an inner tube assembly 402 and an outer tube assembly 408 with interference members. The inner tube assembly 402 includes a inner tube 422, an inner tube hub 404 and an interference member 406, for example, a groove formed on an outer surface of the inner tube hub 404 at a proximal region of the inner tube hub 404. The outer tube assembly 408 includes a outer tube 420, an outer tube hub 410 and an interference member 412, for example, a retaining member that includes an indentation formed on a distal region of and on an outer surface of the outer tube hub 410. The indentation 412 forms a protrusion 414 on an inner surface of the outer tube hub 410 that interferes with the groove 406 to prevent a force applied to the inner tube 422 or the outer tube 420 (or both) from separating the inner and outer tubes without rendering the medical device 100 unusable (for example, as a result of the outer tube assembly 408 breaking in the area with the indentations 412.

Figure 5:
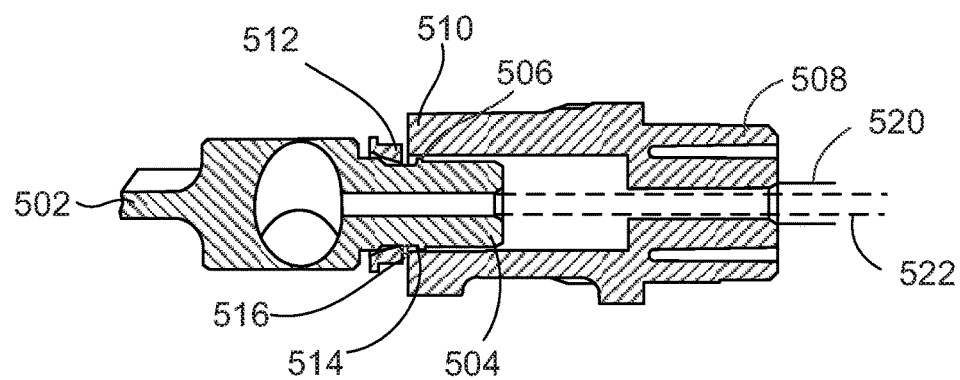
FIG. 5 is cross-sectional view of a third embodiment of an inner tube assembly and an outer tube assembly with interference members.

FIG. 5 is cross-sectional view of a third embodiment of an inner tube assembly 502 and an outer tube assembly 508 with interference members. The inner tube assembly 502 includes a inner tube 522, an inner tube hub 504, and an interference member 506, for example, an inclined ridge formed on a proximal region of and on an outer surface of the inner tube hub 504. The outer tube assembly 508 includes a outer tube 520, an outer tube hub 510, and an interference member 512, for example, a snap mechanism attached to a proximal region of and that protrudes toward an inner portion of the outer tube hub 510.

The snap mechanism 512 and the ridge 506 are each inclined as shown in FIG. 5, and the snap mechanism 512 is additionally elastically deformable. When the inner tube assembly 502 is inserted into the outer tube assembly 508, the ridge 506 elastically deforms the snap mechanism 512 from an initial position to an expanded position thereby accommodating the inner tube hub 504 within the outer tube hub 510. The snap mechanism 512 returns to the initial position once the ridge 506 clears the snap mechanism. An outer diameter of the ridge 506 and a dimension of the snap mechanism 512 can be formed such that the surfaces 514 and 516 on the ridge 506 and the snap mechanism 512, respectively, interfere when a force is applied to remove the inner tube assembly 502 from the outer tube assembly 508, thereby preventing the former assembly from being pulled out of the latter assembly without causing damage to the snap area. When a force is applied to remove the inner tube assembly 502 from the outer tube assembly 508, then the ridge 506 and the snap mechanism 512 engage to oppose the force. A continuous increase in the force can cause damage to or break the snap mechanism 512 rendering the device unusable.

Figure 6:
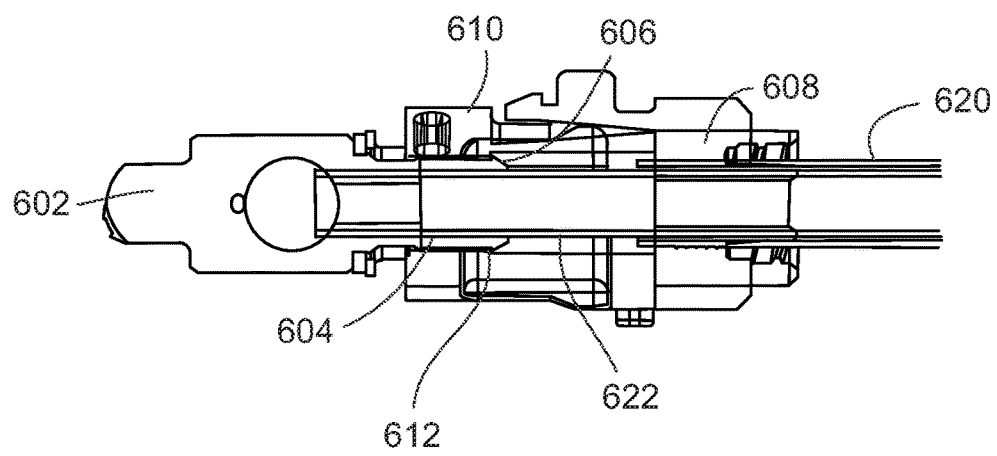
FIG. 6 is cross-sectional view of a fourth embodiment of an inner tube assembly and an outer tube assembly with interference members.

FIG. 6 is cross-sectional view of a fourth embodiment of an inner tube assembly 602 and an outer tube assembly 608 with interference members. The inner tube assembly 602 includes an inner tube 622, an inner tube hub 604, and an interference member 606, for example, a snap mechanism formed on a distal region of and on an outer surface of the inner tube hub 604. The outer tube assembly 608 includes a outer tube 620, an outer tube hub 610, and an interference member 612, for example, a step feature formed on an inner surface of the outer tube hub 610. An outer diameter of the snap mechanism 606 and an inner diameter of the step feature 612 can form surfaces that interfere when the force is applied to remove the inner tube assembly 602 from the outer tube assembly 608. In some implementations, the interfering surfaces can be parallel to each other and perpendicular to an outer surface of the inner and outer tube hubs. An opposing force to separate the inner tube assembly 602 from the outer tube assembly 608 can cause the snap mechanism and the step feature to engage. An increase in the force beyond a threshold can cause damage to or break the snap mechanism rendering the device unusable.

Figure 7:
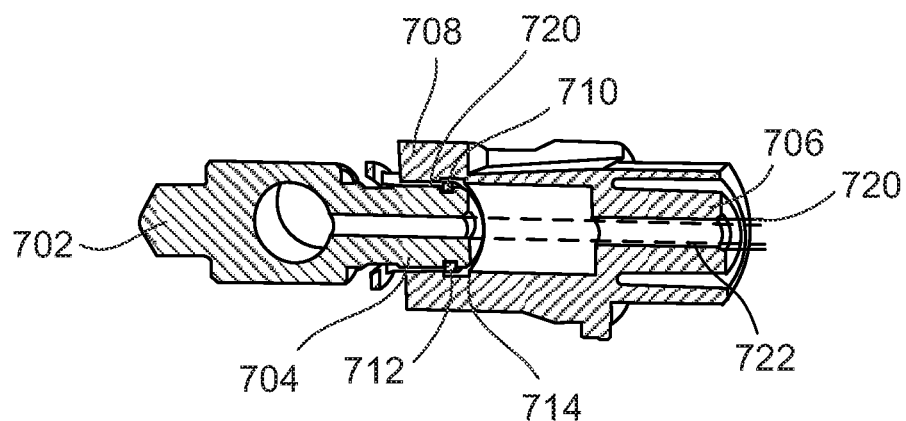
FIG. 7 is cross-sectional view of a fifth embodiment of an inner tube assembly and an outer tube assembly with interference members.
Figure 8:
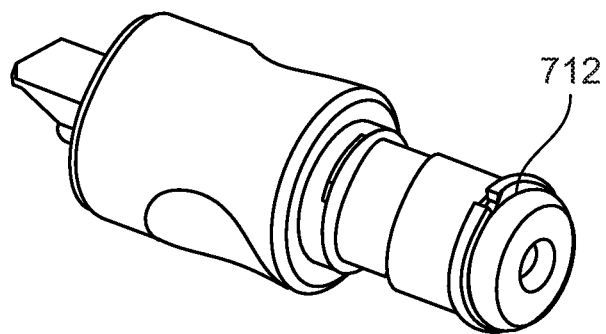
FIG. 8 is an example of a split ring attached to an inner tube hub according to the embodiment shown in FIG. 7.

FIGS. 7 and 8 show a fifth embodiment of an inner tube assembly 702 and an outer tube assembly 706 with interference members. The inner tube assembly 702 and the outer tube assembly 706 include a inner tube 722 and an inner tube hub 704, and a outer tube 720 and an outer tube hub 708, respectively. An interference member 710, for example, a groove is formed on a distal region of and on an outer surface of the inner tube hub 704. A ring 712 is inserted in the groove 710. The ring 712 is configured to compress (for example, radially) to pass through a portion 720 of the outer tube hub 708 to allow the ring 712 to be inserted into the outer tube hub 708. The outer tube assembly 706 includes an interference member 714, for example, another groove that is formed on a proximal region of an on an inner surface of the outer tube hub 708. The portion 720 of the outer tube hub 708 has a dimension (for example, inner diameter) that is smaller than an outer diameter of the ring 712. The ring 712 compresses to enter the outer tube hub 708 and move through the portion 720, and expands into the groove 714. Because the diameter of the uncompressed ring 712 is larger than that of the portion 720, the ring 712 interferes to prevent a force applied along the longitudinal axis from separating the inner and outer tubes without rendering the medical device 100 unusable. In some embodiments, the ring can be a split ring 712, as shown particularly in FIG. 8.

Figure 9:
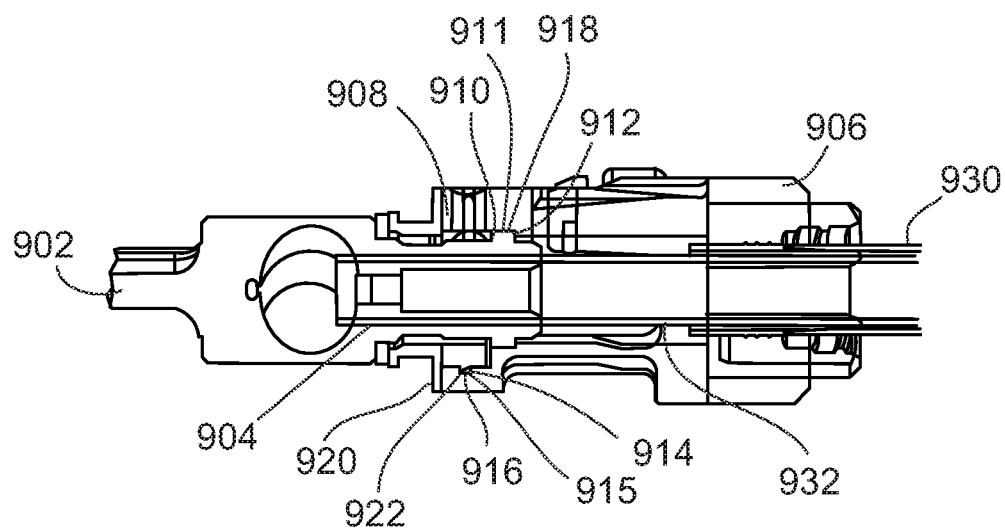
FIG. 9 is cross-sectional view of a sixth embodiment of an inner tube assembly and an outer tube assembly with interference members.
Figure 10:
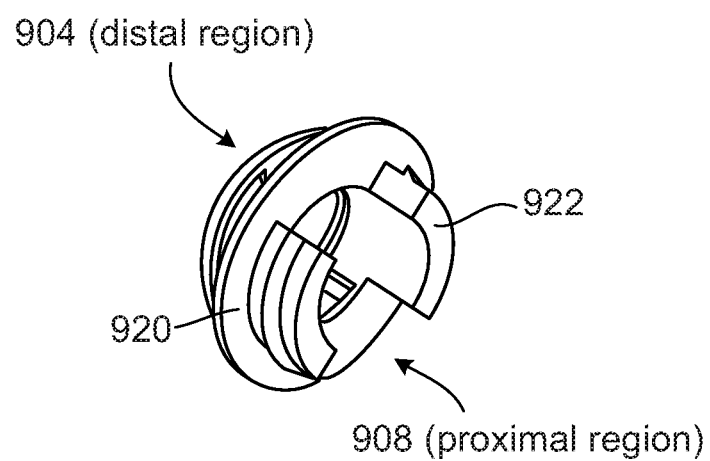
FIG. 10 is an example of a seal flange hub according to the embodiment of FIG. 9.

FIGS. 9 and 10 show a sixth embodiment of an inner tube assembly 902 and an outer tube assembly 906 with interference members. The outer tube assembly 906 includes a outer tube 930, an outer tube hub 908, and multiple interference members. The interference members include step features 910 and 912 that define a first groove 911, and step features 914 and 916 that define a second groove 915. Both grooves are formed on an inner surface of and near a distal region of the outer tube hub 906, with the first groove 911 being farther from the distal region than the second groove 915. The inner tube assembly 902 includes an inner tube hub 904, and an interference member 918, for example, a ridge 918 formed on an outer surface of and at a distal region of the inner tube hub 904.

The device 900 additionally includes a seal flange 920 attached to the outer tube hub 908. The seal flange 920 is coupled to the distal region of the inner tube hub 904, and both are then inserted into the outer tube hub 908. Whereas the inner tube hub 904 can move relative to the outer tube hub 908, the seal flange 920 is stationary relative to the outer tube hub 908, which may simplify the design and yield a greater force to separate the inner and the outer tubes. The seal flange 920 includes a snap feature 922 that snaps into the second groove 915 defined by the step features 914 and 916. The ridge 918 engages the first groove 911 defined by the step features 910 and 912. The snap feature and the ridge interfere with the step features to prevent the force exerted along the longitudinal axis from separating the inner and outer tube assemblies. The portion of the seal flange 920 that includes the snap feature 922 is not a complete circle. This may provide a higher level of flex during insertion, which may allow larger interference members (relative to the other embodiments described) to be used. Larger interference members may provide for a stronger coupling. In some embodiments, the seal flange 920 can include a snap feature, as particularly illustrated in FIG. 10. As an alternative to a snap feature, the seal flange and the outer tube hub can be threaded. The threaded parts or the unthreaded parts or both can be attached using a permanent bond (for example, an adhesive).

Figure 11:
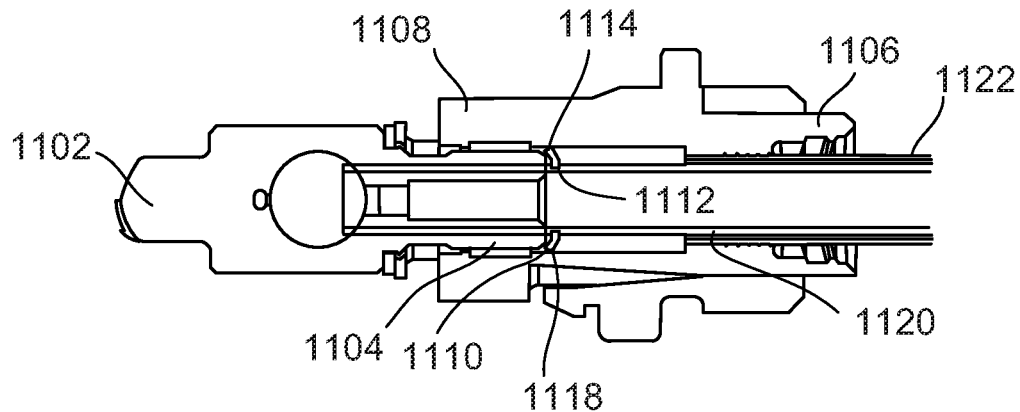
FIG. 11 is cross-sectional view of a seventh embodiment of an inner tube assembly and an outer tube assembly with interference members.

FIG. 11 is cross-sectional view of a seventh embodiment of an inner tube assembly 1102 and an outer tube assembly 1106 with interference members. The inner tube assembly 1102 includes a inner tube 1120, an inner tube hub 1104, and an interference member 1110, for example, a retaining ring. The interference member 1110 also includes a groove 1112 formed on an outer surface of the inner tube hub 1104, in which the retaining ring 1110 is positioned. The outer tube assembly 1106 includes a outer tube 1122 and an outer tube hub 1108. When the inner tube hub 1104, which includes the retaining ring 1110 positioned in the groove 1112, is inserted into the outer tube hub 1108, the retaining ring 1110 flexes to allow insertion. When a force is exerted on the inner tube hub 1104 in a direction opposite to the direction of insertion, the retaining ring 1110 bows backward while an edge 1118 of the retaining ring interferes with an inner wall 1114 of the outer tube hub 1108 and prevents the force from separating the inner and outer assemblies.

Figure 12:
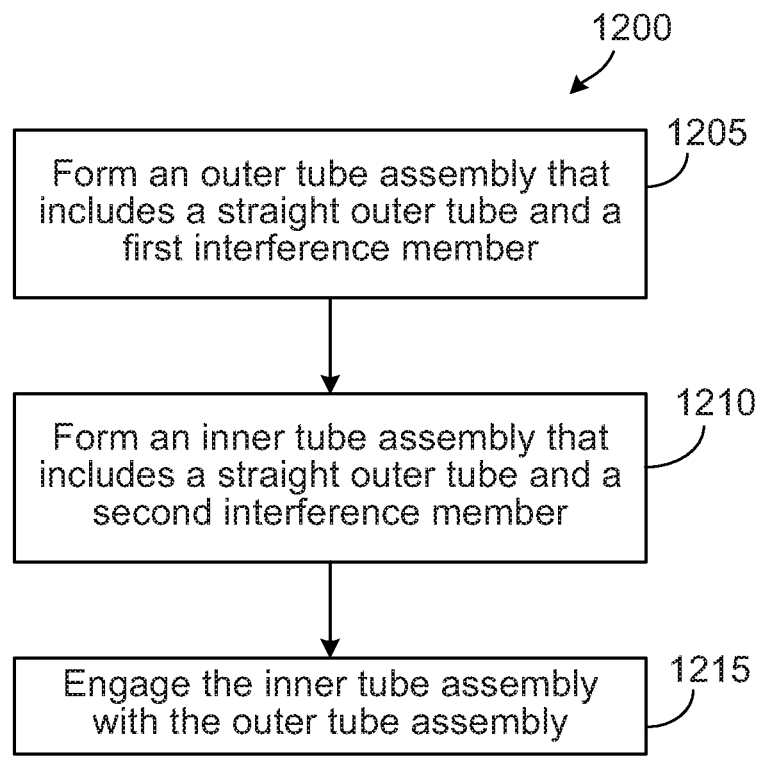
FIG. 12 is a flowchart of an example of a process for producing a medical device.

FIG. 12 is a flowchart of an example of a process 1200 for producing a medical device. The process 1200 includes forming an outer tube assembly that includes a outer tube and a first interference member (1205). The process 1200 includes forming an inner tube assembly that includes a inner tube and a second interference member (1210). The process 1200 includes engaging the inner tube assembly with the outer tube assembly such that the inner tube is disposed within the outer tube (1215). The inner tube and the outer tube are configured to rotate relative to each other to resect tissue at a distal region of the inner tube and outer tubes. The first and second interference members are configured to prevent a force exerted along a longitudinal axis of the inner tube from separating the inner and outer tubes without rendering the medical device unusable. Examples of the inner tube assembly and the outer tube assembly are described above with reference to FIGS. 3-10.

In various embodiments, when producing a medical device such as the one shown in FIG. 3, forming the inner tube assembly that includes the inner tube and the second interference member includes forming a groove on an outer surface of the inner tube hub. Forming the outer tube assembly that includes the outer tube and the first interference member includes forming one or more holes through the outer tube hub. Engaging the inner tube assembly with the outer tube assembly such that the inner tube is disposed within the outer tube includes extending at least one retaining member through the one or more holes in the outer tube hub to interfere with the groove to prevent the force from separating the inner and outer tubes.

When producing a medical device such as the one shown in FIG. 4, forming the inner tube assembly that includes the inner tube and the second interference member includes forming a groove on an outer surface of the inner tube hub. Forming the outer tube assembly that includes the outer tube and the first interference member includes forming an indentation on an outer surface of the outer tube hub. The indentation forms a protrusion on an inner surface of the outer tube hub. Engaging the inner tube assembly with the outer tube assembly such that the inner tube is disposed within the outer tube includes engaging the indentation and the groove such that the protrusion interferes with the groove to prevent the force from separating the inner and outer tubes.

When producing a medical device such as the one shown in FIG. 5, forming the inner tube assembly that includes the inner tube and the second interference member includes forming an inclined ridge on an outer surface of the inner tube hub. Forming the outer tube assembly that includes the outer tube and the first interference member includes forming a snap mechanism that protrudes toward an inner portion of the outer tube hub. Engaging the inner tube assembly with the outer tube assembly such that the inner tube is disposed within the outer tube includes inserting the inclined ridge past the snap mechanism such that the inclined ridge interferes with the snap mechanism to prevent the force from separating the inner and outer tubes.

When producing a medical device such as the one shown in FIG. 6, forming the inner tube assembly that includes the inner tube and the second interference member includes forming a snap mechanism on an outer surface of the inner tube hub. Forming the outer tube assembly that includes the outer tube and the first interference member includes forming a step feature on an inner surface of the outer tube hub. Engaging the inner tube assembly with the outer tube assembly such that the inner tube is disposed within the outer tube includes inserting the snap mechanism past the step feature such that the snap mechanism interferes with the step feature to prevent the force from separating the inner and outer tubes.

When producing a medical device such as the one shown in FIG. 7, forming the inner tube assembly that includes the inner tube and the second interference member includes forming a first groove on an outer surface of the inner tube hub. Forming the outer tube assembly that includes the outer tube and the first interference member includes forming a second groove on an inner surface of the outer tube hub. Engaging the inner tube assembly with the outer tube assembly such that the inner tube is disposed within the outer tube includes attaching a compressible ring to the first groove and inserting the inner tube assembly into the outer tube assembly such that the ring expands into the second groove and interferes to prevent the force from separating the inner and outer tubes.

When producing a medical device such as the one shown in FIG. 9, forming the inner tube assembly that includes the inner tube and the second interference member includes forming a ridge on an outer surface of the inner tube hub. Forming the outer tube assembly that includes the outer tube and the first interference member includes forming a plurality of step features on an inner surface of the outer tube hub. Engaging the inner tube assembly with the outer tube assembly such that the inner tube is disposed within the outer tube includes attaching a seal flange to the inner tube hub and inserting at least a portion of the inner tube assembly into the outer tube assembly such that the ridge engages a first step feature and the seal flange engages a second step feature, and interfere to prevent the force from separating the inner and outer tubes.

When producing a medical device such as the one shown in FIG. 11, forming the inner tube assembly that includes the inner tube and the second interference member includes forming a groove on an outer surface of the inner tube hub. Forming the outer tube assembly that includes the outer tube and the first interference member includes forming an inner wall in the outer tube hub. Engaging the inner tube assembly with the outer tube assembly such that the inner tube is disposed within the outer tube comprises attaching a retaining ring that includes an edge to the groove and inserting the inner tube assembly into the outer tube assembly such that the edge interferes with the outer tube hub to prevent the force from separating the inner and outer tubes.

While this specification contains many specific implementation details, these should not be construed as limitations on the scope of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Thus, particular embodiments of the subject matter have been described. Other embodiments are within the scope of the following claims.

What is claimed is:

1. A method of producing a medical device, the method comprising:
    forming an outer tube assembly that includes a straight outer tube and an outer tube hub and a first interference member comprising a snap mechanism that protrudes toward an inner portion of the outer tube hub, the outer tube coupled to the outer tube hub at a proximal region of the outer tube;
    forming an inner tube assembly that includes a straight inner tube and an inner tube hub defining an aspiration lumen and a second interference member comprising a ridge on an outer surface of the inner tube hub, the inner tube hub at least partially disposed within the outer tube hub, the inner tube coupled to the inner tube hub at a proximal region of the inner tube; and
    engaging the inner tube assembly with the outer tube assembly such that the inner tube is disposed within the outer tube, wherein the inner tube and the outer tube are configured to rotate relative to each other when engaged, and the first and second interference members are configured to interact with each other when the inner and outer tubes are engaged to prevent a force exerted along a longitudinal axis of the inner tube from separating the inner and outer tubes without rendering the medical device unusable by breaking or causing damage to the first interference member.

2. The method of claim 1, wherein the step of forming the inner tube assembly that includes the straight inner tube and the inner tube hub defining the aspiration lumen and the second interference member comprising the ridge on the outer surface of the inner tube hub includes forming the ridge on the outer surface of the inner tube hub, the step of forming the outer tube assembly that includes the straight outer tube and the outer tube hub and the first interference member comprising the snap mechanism that protrudes toward the inner portion of the outer tube hub comprises forming the snap mechanism that protrudes toward the inner portion of the outer tube hub, and engaging the inner tube assembly with the outer tube assembly such that the inner tube is disposed within the outer tube comprises inserting the ridge past the snap mechanism such that the ridge interferes with the snap mechanism to prevent the force from separating the inner and outer tubes.

3. The method of claim 1, further comprising: attaching the inner tube hub to a proximal end of the inner tube, the inner tube hub having an extension, wherein the extension is configured to couple the inner tube assembly and the inner tube hub to a drive unit configured to rotate the inner tube and outer tube relative to each other.

4. The method of claim 1, further including the step of elastically deforming the snap mechanism to accommodate the ridge in response to the at least the portion of the inner tube assembly being inserted into the outer tube assembly.

5. The method of claim 1, wherein the outer tube includes an opening at a distal end, the method further including the step of forming a burr at a distal end of the inner tube to resect tissue.

6. The method of claim 1, further including the steps of:
    forming a first cutting surface on a distal end of the outer tube; and
    forming a second cutting surface on a distal end of the inner tube configured to cooperate with the first cutting surface to resect tissue.

7. The method of claim 1, further including the step of forming a latching mechanism for connection to a handpiece in the outer hub.

8. The method of claim 7, further including the step of engaging an annular flange of the handpiece with ramped latches of a cantilevered resilient arm of the latching mechanism.

* * * * *